(12) United States Patent
Kang et al.

(10) Patent No.: US 9,706,928 B2
(45) Date of Patent: *Jul. 18, 2017

(54) DYNAMIC OPTICAL HEAD AND IMAGING DEVICE USING FLEXIBLE NANO FILM OPTICAL STRUCTURE

(71) Applicant: INDUSTRY-ACADEMIC COOPERATION FOUNDATION YONSEI UNIVERSITY, Seoul (KR)

(72) Inventors: Shinill Kang, Seoul (KR); Jungjin Han, Seoul (KR); Eikhyun Cho, Seoul (KR); Jongmyeong Shim, Seoul (KR); Wonjoon Choi, Seoul (KR); Seok-min Kim, Seoul (KR); Dong Hyun Kim, Seoul (KR); Chulmin Joo, Goyang-si (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 103 days.

This patent is subject to a terminal disclaimer.

(21) Appl. No.: 14/719,904

(22) Filed: May 22, 2015

(65) Prior Publication Data
US 2015/0338267 A1 Nov. 26, 2015

(30) Foreign Application Priority Data
May 23, 2014 (KR) ........................ 10-2014-0062632

(51) Int. Cl.
*G01J 3/44* (2006.01)
*A61B 5/00* (2006.01)
(Continued)

(52) U.S. Cl.
CPC .......... *A61B 5/0075* (2013.01); *A61B 5/0071* (2013.01); *G01J 1/42* (2013.01);
(Continued)

(58) Field of Classification Search
CPC . G01Q 70/06; B82Y 20/00; G01J 1/42; G01J 3/44; G01J 3/4412
(Continued)

(56) References Cited

U.S. PATENT DOCUMENTS 6,541,755 B1 * 4/2003 Fujita ..................... B82Y 20/00
250/214.1
9,291,642 B2 * 3/2016 Kang ..................... G01Q 60/22

FOREIGN PATENT DOCUMENTS

JP 2001-066783 A 3/2001
JP 2003-091816 A 3/2003
(Continued)

*Primary Examiner* — Que T Le
(74) *Attorney, Agent, or Firm* — LRK Patent Law Firm

(57) ABSTRACT

The present invention relates to an optical head for revealing near field through beams irradiated from a light source of a far field optical system, the optical head including: a flexible substrate made of a soft material and adapted to allow the optical head to be brought into close contact with a measured object and attached thereto even if the measured object has a curved or flat surface; and a near-field revelation part located between the measured object and the flexible substrate in such a manner as to have one side brought into contact with the flexible substrate and the other side detachably attached to the measured object and adapted to reveal the near field through the beams irradiated from the light source.

52 Claims, 11 Drawing Sheets

(51) Int. Cl.
    *G01J 1/42*     (2006.01)
    *G01Q 60/22*     (2010.01)
    *G01Q 70/06*     (2010.01)

(52) U.S. Cl.
    CPC ............ G01J 3/4412 (2013.01); G01Q 60/22 (2013.01); *A61B 2562/146* (2013.01); *A61B 2562/164* (2013.01); *G01J 3/44* (2013.01); *G01Q 70/06* (2013.01); *Y10S 977/954* (2013.01)

(58) Field of Classification Search
    USPC .............. 250/216, 201.3, 226, 239, 306–311
    See application file for complete search history.

(56) References Cited

FOREIGN PATENT DOCUMENTS

| | | |
|---|---|---|
| JP | 2007-322396 A | 12/2007 |
| JP | 2008-077732 A | 4/2008 |
| JP | 2011-526069 A | 9/2011 |
| JP | 2011-210306 A | 10/2011 |
| KR | 10-2005-0110083 A | 11/2005 |
| KR | 10-2012-0076119 A | 7/2012 |

\* cited by examiner

DYNAMIC OPTICAL HEAD AND IMAGING DEVICE USING FLEXIBLE NANO FILM OPTICAL STRUCTURE

BACKGROUND OF THE INVENTION

Field of the Invention

The present invention relates to an optical head and an imaging device, and more particularly, to an optical head and an imaging device using a flexible nano layer for formation of dynamic nano aperture.

Background of the Related Art

Nano convergence market has been expanding rapidly at an annual growth rate of 21.3% from 835.4 billion dollars in 2013 and is expected to reach 1 trillion, 974.9 billion dollars by 2017. When considering that nano technology is not commercialized yet, economical and industrial values of the nano technology will become great in the future.

Further, nanoimaging technology may be utilized in bio/medical fields as well as nano-device field. As medical paradigm is shifted from treatment to prevention, the demand for disease prediction technology through neuron signal transmission system analysis and molecule/bacteria imaging is drastically increased, and the mass production of technologies and products with which in-vivo diagnosis can be performed is required over the whole world.

The nanoimaging technology can be applied to a variety of fields. Referring first to the bio field, the most desirable measurement method for the understanding of body phenomenon in biology and medical research is performed on in-vivo measurement, and so as to acquire more detailed body information through the in-vivo measurement, an endoscope system, in which a confocal microscope, an optical coherence tomography, and a ultrasonic microscopy are adopted, is developed and used upon the in-vivo measurement and analysis of the body phenomenon. The measurement techniques applied to the current endoscope system have respective advantages and disadvantages, and further, it is hard for them to conduct precise analysis in the in-vivo state due to their limitation in resolution.

So as to analyze molecule-scale variations generated in cell units and cells, an image can be made in a small field of view and with ultra-high resolution through nanoimaging technology like AFM and NSOM, but there is a limit in imaging speed, so that it is impossible to perform in-vivo nanoimaging for various functional variations and interactions in cells or among cells distributed in a large area.

If the type of disease and the treatment method are selected through fine tissue analysis in the process where the disease is diagnosed and treated, currently, a cell tissue is picked and the in-vitro analysis for the cell tissue is conducted through an external measurement system.

In case of the diagnosis of the disease through the in-vitro analysis, however, it is hard to provide the diagnosed result rapidly and further to measure the response in the body in real time.

When current nanoimaging technology is applied to the in-vivo measurement, on the other hand, there is another big problem in that a sample does not have any flat shape and further works in real time. The current nanoimaging technology allows the measurement of the sample to be conducted in the state of maintaining a given gap from the sample and continuously connects very small fields of view to form one image. Since a measured object in the body is kept working, in this case, the existing nanoimaging technology having a slow frame rate cannot acquire accurate real-time images, and when curved-shaped body tissues kept working are measured, further, it is impossible to maintain a given gap from the body tissues accurately.

In case of display field, substrate sizes have been increased day by day, and now, mass production for tenth generation substrates (3080 mm×2500 mm) has been conducted. Further, large-area substrate trend will be kept for a period of time. In addition to the large area, on the other hand, the number of high resolution display products in the display field has been increased by the demand of consumers, and the market share of products having 400 ppi or more is expected to increase. Accordingly, the demand in industrial fields for the mass production of the large-area high-speed and high-resolution on-machine inspection equipment as well as semiconductor inspection equipment is expected to increase rapidly.

Recent subjects of the research and development of electronic devices like semiconductors and displays are high integration, large area and flexibility. In addition to the semiconductor field in which nano-scale patterns are already applied, ultra high density (UHD) display technology is applied in the display field, so that the nano-scale patterns will be adopted in the display field. Accordingly, there is a need for development of on-machine nanoimaging technology capable of conducting total inspection on the nano-scale patterns every process.

Commercial optical inspection/measurement equipment has a resolution of micrometer units, so that the equipment is utilized in the on-machine imaging process in the current display field, but it is not utilized in the semiconductor process having the nano-scale units. Further, the degree of utilization of the equipment in the display field will be decreased. There are SEM, AFM and NSOM as current nano-scale inspection equipment, but they have many limitations in application to on-machine imaging.

Particularly, it is hard that flexible electronic devices like flexible display, wearable computer and so on are applied to the existing fixed focus type imaging inspection system due to the flexibility of the substrate.

The most important key point for enhancing the energy efficiency in the nano-energy field where nano materials/devices are applied is to desirably design the diffusion lengths of the excitons and charges on the active layer of solar cells and on the battery electrodes. However, most of research conducted until now just measures the diffusion lengths in an indirect way (indirect calculation through photocurrent measurement or spectra measurement), so that the measurement is under the influence of the measurement environments and the surrounding materials constituting the devices, thus making it hard to conduct the measurement accurately.

Recently, technologies capable of measuring the diffusion lengths in a direct way through source lasers, like scanning photocurrent microscopy (laser-beam induced current technique) and scanning laser-spot technique, have been developed, and they can be utilized in the desirable combination and design of nano materials and devices. In the nano-energy field where the nano materials and devices are applied, however, the exiting technologies have had many restrictions in manufacturing the large area imaging device and measuring the uniformity of the diffusion lengths.

As the nano convergence technologies have been rapidly developed, as mentioned above, the measurement and analysis of the nano-scale structures and physical phenomenon are needed in various fields, and the nano-scale measurement technologies, such as, SEM, AFM, TEM, NSOM and so on have been developed very rapidly. Among the various nano-scale measurement technologies, the technology capable of conducting the in-situ/on-machine/in-vivo measurements is optical nanoimaging, and a near-field optical system like NSOM is used as the existing optical nanoimaging technology.

However, the optical imaging system using near field requires the control of a gap of tens of nanometers, thus making it hard to be applied to a parallel optical system. Accordingly, the optical imaging system using near field has limitations in large area imaging, and it is impossible to conduct the imaging for a sample having a curved shape.

FIG. 1 is a perspective view showing near-field nanoimaging, and FIG. 2 is a sectional view showing near-field nanoimaging wherein probes are connected in parallel to each other.

As shown in FIG. 1, near-field nanoimaging has a limit in the application of large area imaging due to a small imaging area, and further, a gap (tens of nanometers) should be maintained for the imaging.

So as to overcome the small imaging area as shown in FIG. 1, FIG. 2 shows probes connected in parallel to each other. In this case, however, if a measured object has a curved shape, an area on which near-field light is revealed and an area on which near-field light is not revealed are generated together, thus making it hard to obtain uniform imaging. So as to apply the near-field nanoimaging to the large area, that is, the uniform imaging for the measured object should be achieved, and accordingly, the conventional near-field nanoimaging has a limit in the shapes of the measured object.

SUMMARY OF THE INVENTION

Accordingly, the present invention has been made in view of the above-mentioned problems occurring in the prior art, and it is an object of the present invention to provide an optical head and an imaging device using a flexible nano layer for formation of dynamic nano aperture wherein near field is revealed by using a near-field revelation part, thus making it possible to conduct high resolution, and wherein a flexible substrate is flexibly deformed in such a manner as to be easily brought into close contact with a measured object even if the measured object has a curved or flat shape, thus solving the existing gap-maintaining problem.

It is another object of the present invention to provide an optical head and an imaging device using a flexible nano layer for formation of dynamic nano aperture wherein a near-field revelation part includes a layer for formation of dynamic optical nano apertures or a metal nano structure, so that within the focal region of far field optics, it is possible to reveal near field through the change of a material for formation of dynamic optical nano apertures from optically non-transparent phase to optically transparent phase or through the localized surface plasmon effects of the nano structure formed on the near-field revelation part.

It is yet another object of the present invention to provide an optical head and an imaging device using a flexible nano layer for formation of dynamic nano aperture wherein the optical head includes a nano lubricating layer formed on the underside thereof to prevent friction and contamination of a measured object.

It is still another object of the present invention to provide an optical head and an imaging device using a flexible nano layer for formation of dynamic nano aperture wherein the imaging device is provided with a multi light array, thus making it possible to conduct large area imaging.

It is yet still another object of the present invention to provide an optical head and an imaging device using a flexible nano layer for formation of dynamic nano aperture wherein a multi-light array and the optical head are coupled integrally with each other, and through the coupling, the region of the light collected on a photo detector becomes expanded, thus allowing the imaging device to be easily applied to a measured object having a large curved angle.

It is yet another object of the present invention to provide an optical head and an imaging device using a flexible nano layer for formation of dynamic nano aperture wherein the light reflected from a measured object is detected through a photo detector, and if the light is not reflected from the measured object whose thickness is relatively low, the photo detector is located below the measured object, thus detecting the light passing through the measured object.

It is still another object of the present invention to provide an optical head and an imaging device using a flexible nano layer for formation of dynamic nano aperture wherein the light reflected or scattered from a measured object, the fluorescence signal generated from the measured object, or non-linear optical signal (for example, Raman scattering, two-photon fluorescence, or second harmonic generation) is detected through a multi-light array and a photo detector.

It is still yet another object of the present invention to provide an optical head and an imaging device using a flexible nano layer for formation of dynamic nano aperture wherein a photo detector is located below a measured object if necessary, thus detecting the light transmitted to or scattered from the measured object, the fluorescence signal generated from the measured object, or non-linear optical signal (for example, Raman scattering, two-photon fluorescence, or second harmonic generation).

To accomplish the above-mentioned objects, according to a first aspect of the present invention, there is provided an optical head for revealing near field through beams irradiated from a light source of a far field optical system, the optical head including: a flexible substrate made of a soft material and adapted to allow the optical head to be brought into close contact with a measured object and attached thereto even if the measured object has a curved or flat surface; and a near-field revelation part located between the measured object and the flexible substrate in such a manner as to have one side brought into contact with the flexible substrate and the other side detachably attached to the measured object and adapted to reveal the near field through the beams irradiated from the light source, wherein the near-field revelation part includes: a layer for formation of dynamic optical nano apertures; a first dielectric protective layer formed on top of the layer for formation of dynamic optical nano apertures to prevent the generation of degradation and mixing caused by the inter-diffusion between the layer for formation of dynamic optical nano apertures and the flexible substrate; and a second dielectric protective layer formed on the underside of the layer for formation of dynamic optical nano apertures to maintain a given distance between the layer for formation of dynamic optical nano apertures and the measured object.

To accomplish the above-mentioned objects, according to a second aspect of the present invention, there is provided an optical head for revealing near field through beams irradiated from a light source of a far field optical system, the optical head including: a flexible substrate made of a soft material and adapted to allow the optical head to be brought into close contact with a measured object and attached thereto even if the measured object has a curved or flat surface; and a near-field revelation part located between the measured object and the flexible substrate in such a manner as to have one side brought into contact with the flexible substrate and the other side detachably attached to the measured object and adapted to reveal the near field through the beams irradiated from the light source, wherein the near-field revelation part includes a nano-structure array.

According to the present invention, desirably, the optical system includes any one selected from the group consisting of a macro optical system, a hologram light modulator, a DMD mirror, a microlens array, and a scanner.

According to the present invention, desirably, the flexible substrate and the near-field revelation part are formed integrally with each other.

According to the present invention, desirably, the nano-structure array includes any one selected from the group consisting of a nano-hole array, a nano-island array, a nano-pillar array, a nano-line array, and a nano-dot array.

According to the present invention, desirably, the nano-structure array includes a metal array formed of any one selected from the group consisting of Au, Ag, Pt, Cr and Al.

According to the present invention, desirably, the near-field revelation part includes a flexible nano film.

According to the present invention, desirably, the layer for formation of dynamic optical nano apertures is made of a chalcogenide-based material.

According to the present invention, desirably, the layer for formation of dynamic optical nano apertures is made of AgOx or PtOx.

According to the present invention, desirably, the first dielectric protective layer and the second dielectric protective layer are made of an oxide-based material, a nitride-based material, a carbide-based material, or a chalcogenide-based material.

According to the present invention, desirably, the oxide-based material includes any one selected from the group consisting of SiOx, ZnS—SiOx, GeOx, AlOx, BeOx, ZrOx, BaTiOx, SrTiOx, and TaOx.

According to the present invention, desirably, the nitride-based material includes any one selected from the group consisting of SiNx, BNx, and AlNx.

According to the present invention, desirably, the carbide-based material includes SiC.

According to the present invention, desirably, the chalcogenide-based material includes any one selected from the group consisting of ZnS and ZnSe.

According to the present invention, desirably, flexible substrate includes any one selected from the group consisting of PC, COP, PI, PET, OPP, PE, PP, PMMA, and acrylic films, or any one selected from the group consisting of sodalime glass, borosilicate glass, fused silica glass, quartz glass, and biocompatible polymers (such as PLA, PGA, PLGA, LPLA, DUPLA, PCL, PDO and PDMS).

According to the present invention, desirably, the first dielectric protective layer has a thickness in the range of 30 to 500 nm, the layer for formation of dynamic optical nano apertures has a thickness in the range of 5 to nm, and the second dielectric protective layer has a thickness in the range of 5 to 60 nm.

According to the present invention, desirably, the films have a thickness in the range of 0.04 to 500 um.

According to the present invention, desirably, the optical head further includes a nano lubricating layer formed on the underside thereof to prevent friction and contamination of the measured object.

To accomplish the above-mentioned objects, according to a third aspect of the present invention, there is provided a near-field optical imaging device including: a light source irradiating light; a relay lens unit having one or more lenses adapted to pass the light transmitted to a measured object or reflected on the measured object therethrough and to focus the light irradiated from the light source; a multi-light array adapted to allow the light focused by the relay lens unit to be incident thereon; an optical head adapted to reveal near field on the beams irradiated from the light source of a far-field optical system passing through the multi-light array; and a photo detector adapted to detect the light reflected from the measured object, wherein the optical head includes: a flexible substrate made of a soft material and adapted to allow the optical head to be brought into close contact with the measured object and attached thereto even if the measured object has a curved or flat surface; and a near-field revelation part located between the measured object and the flexible substrate in such a manner as to have one side brought into contact with the flexible substrate and the other side detachably attached to the measured object and adapted to reveal the near field through the beams irradiated from the light source.

According to the present invention, desirably, the multi-light array includes any one selected from the group consisting of a macro optical system, a hologram light modulator, a DMD mirror, a microlens array, and a scanner.

According to the present invention, desirably, the flexible substrate and the near-field revelation part are formed integrally with each other.

According to the present invention, desirably, the near-field revelation part includes a nano-structure array.

According to the present invention, desirably, the nano-structure array includes any one selected from the group consisting of a nano-hole array, a nano-island array, a nano-pillar array, a nano-line array, and a nano dot array.

According to the present invention, desirably, the nano-structure array includes a metal array formed of any one selected from the group consisting of Au, Ag, Pt, Cr and Al.

According to the present invention, desirably, the near-field revelation part includes a flexible nano film.

According to the present invention, desirably, the flexible nano film includes: a first dielectric protective layer formed on top of thereof; a second dielectric protective layer formed on the underside thereof; and a layer for formation of dynamic optical nano apertures formed between the first dielectric protective layer and the second dielectric protective layer.

According to the present invention, desirably, the layer for formation of dynamic optical nano apertures is made of a chalcogenide-based material.

According to the present invention, desirably, the layer for formation of dynamic optical nano apertures is made of AgOx or PtOx.

According to the present invention, desirably, the first dielectric protective layer and the second dielectric protective layer are made of an oxide-based material, a nitride-based material, a carbide-based material, or a chalcogenide-based material.

According to the present invention, desirably, the oxide-based material includes any one selected from the group consisting of SiOx, ZnS—SiOx, GeOx, AlOx, BeOx, ZrOx, BaTiOx, SrTiOx, and TaOx.

According to the present invention, desirably, the nitride-based material includes any one selected from the group consisting of SiNx, BWx, and AlNx.

According to the present invention, desirably, the carbide-based material includes SiCx.

According to the present invention, desirably, the chalcogenide-based material includes any one selected from the group consisting of ZnS and ZnSe.

According to the present invention, desirably, the flexible substrate includes any one selected from the group consisting of PC, COP, PI, PET, OPP, PE, PP, PMMA, and acrylic films, or any one selected from the group consisting of sodalime glass, borosilicate glass, fused silica glass, quartz glass, and biocompatible polymers (such as PLA, PGA, PLGA, LPLA, DUPLA, PCL, PDO and PDMS).

According to the present invention, desirably, the first dielectric protective layer has a thickness in the range of 30 to 500 nm, the layer for formation of dynamic optical nano apertures has a thickness in the range of 5 to 30 nm, and the second dielectric protective layer has a thickness in the range of 5 to 60 nm.

According to the present invention, desirably, the films have a thickness in the range of 0.04 to 500 um.

According to the present invention, desirably, the near-field optical imaging device further includes a nano lubricating layer formed on the underside of the optical head to prevent friction and contamination of the measured object.

According to the present invention, desirably, the multi-light array and the optical head are formed integrally with each other.

According to the present invention, desirably, the photo detector measures Raman scattering generated from the measured object.

According to the present invention, desirably, the photo detector includes a spectrometer in such a manner as to be applied to Raman spectroscopy through the spectrum of the Raman scattering.

According to the present invention, desirably, the photo detector measures two-photon fluorescence and second harmonic generation from the measured object.

According to the present invention, desirably, the photo detector includes a cut-off filter adapted to cut off excitation light to measure the two-photon fluorescence from the measured object.

According to the present invention, desirably, the photo detector is located below the measured object to detect the light passing through the measured object.

According to the present invention, desirably, the photo detector includes a spectrometer in such a manner as to be applied to infrared spectroscopy through the spectrum of the transmitted light.

According to the present invention, desirably, the photo detector is located below the measured object to detect Raman scattering from the measured object.

According to the present invention, desirably, the photo detector includes a spectrometer in such a manner as to be applied to Raman spectroscopy through the spectrum of the Raman scattering.

According to the present invention, desirably, the photo detector is located below the measured object to detect two-photon fluorescence from the measured object.

According to the present invention, desirably, the photo detector includes a cut-off filter adapted to cut off excitation light to measure the two-photon fluorescence from the measured object.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIGS. 11A to 11C are sectional views showing a multi-light array applied to the near-field optical imaging device according to the present invention, wherein FIG. 11a shows a macro optical system, FIG. 11b a hologram light modulator, and FIG. 11c a microlens array;

DETAILED DESCRIPTION OF THE PREFERRED EMBODIMENTS

Hereinafter, an explanation on an optical head and an imaging device using a flexible nano layer for formation of dynamic nano aperture according to the present invention will be in detail given with reference to the attached drawing.

Figure 1:
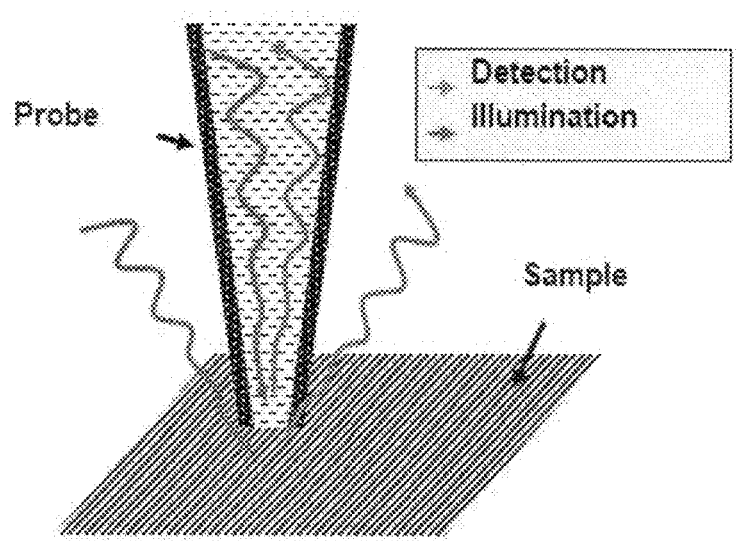
FIG. 1 is a perspective view showing near-field nanoimaging.
Figure 2:
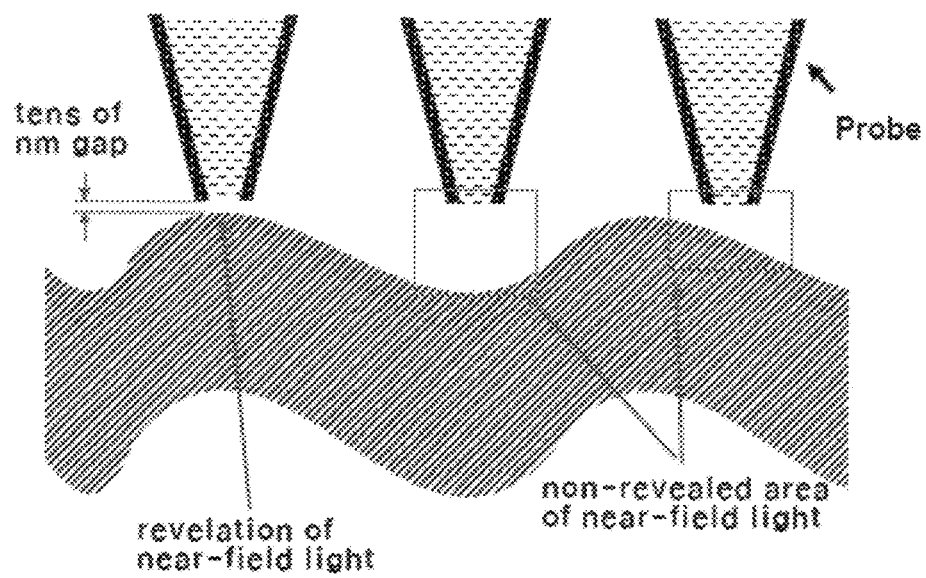
FIG. 2 is a sectional view showing near-field nanoimaging wherein probes are connected in parallel to each other.
Figure 3:
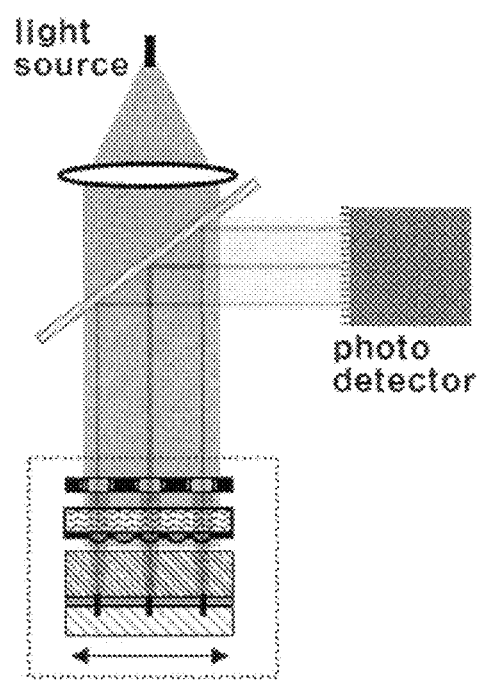
FIG. 3 is a sectional view showing a near-field optical imaging device according to the present invention.
Figure 4:
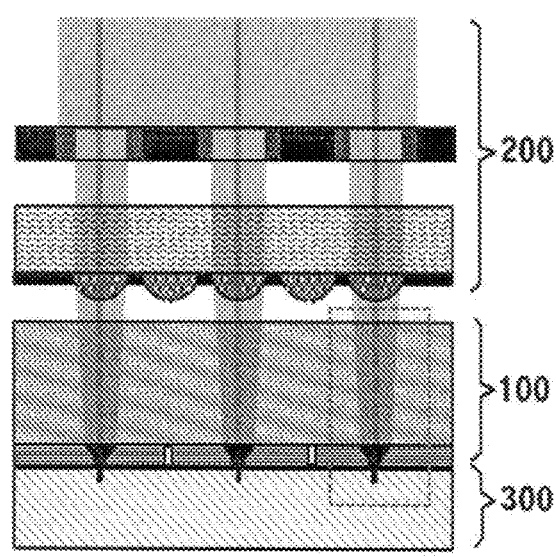
FIG. 4 is a sectional view showing the concept of the near-field imaging according to the present invention.
Figure 5:
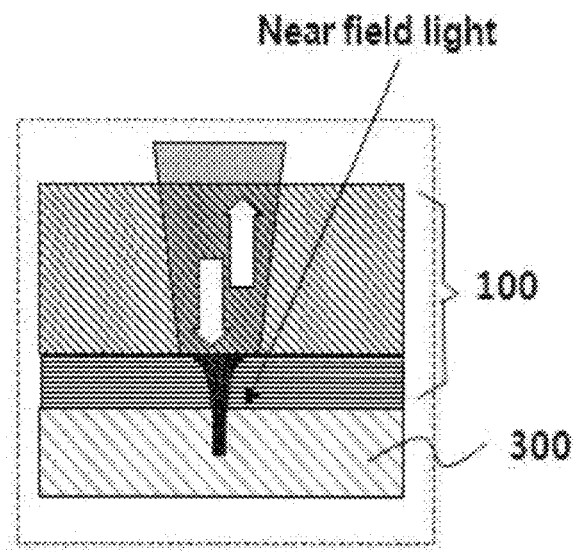
FIG. 5 is an enlarged sectional view showing high resolution imaging implementation through a near-field optical structure according to the present invention.

FIG. 3 is a sectional view showing a near-field optical imaging device according to the present invention, FIG. 4 is a sectional view showing the concept of the near-field imaging according to the present invention, and FIG. 5 is an enlarged sectional view showing high resolution imaging implementation through a near-field optical structure according to the present invention.

As shown in FIGS. 3 to 5, a near-field optical imaging device includes a light source irradiating light therefrom, a relay lens unit having one or more lenses adapted to pass the light transmitted to a measured object 300 or reflected from the measured object 300 therethrough and to focus the light irradiated from the light source thereon, a multi-light array 200 adapted to allow the light focused by the relay lens unit to be incident thereon, an optical head 100 adapted to reveal near field on the beam irradiated from the light source of a far-field optical system passing through the multi-light array 200, and a photo detector adapted to detect light from the measured object 300.

The optical head 100, which reveals near field on the beam irradiated from the light source of the far-field optical system passing through the multi-light array 200, includes a flexible substrate 110 adapted to allow the optical head 100 to be brought into close contact with the measured object 300 even if the outer shape of the measured object 300 is curved or flat and a near-field revelation part located on the flexible substrate 110 to reveal the near field on the beam irradiated from the light source.

Further, the near-field revelation part is a nano-structure array or a flexible nano film.

Figure 6:
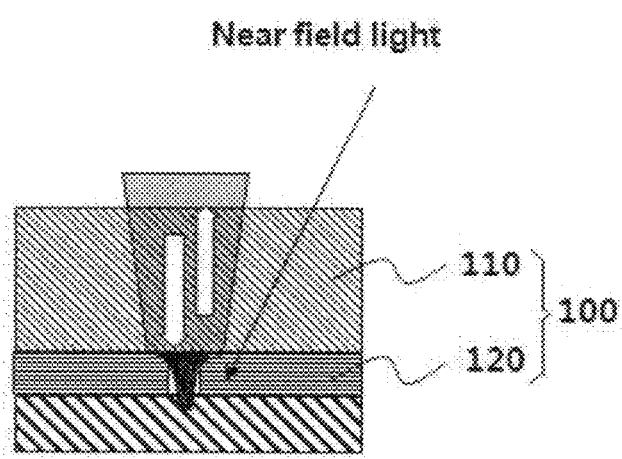
FIG. 6 is a sectional view showing an optical head having a nano-hole structure according to the present invention.
Figure 7:
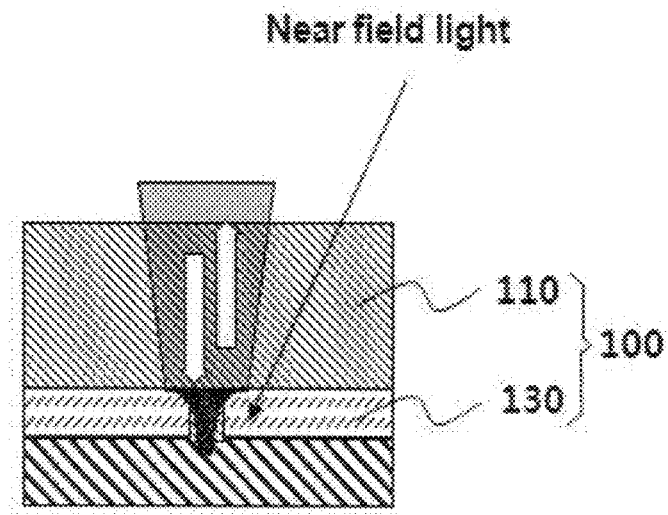
FIG. 7 is a sectional view showing an optical head having a nano-dot structure according to the present invention.
Figure 8:
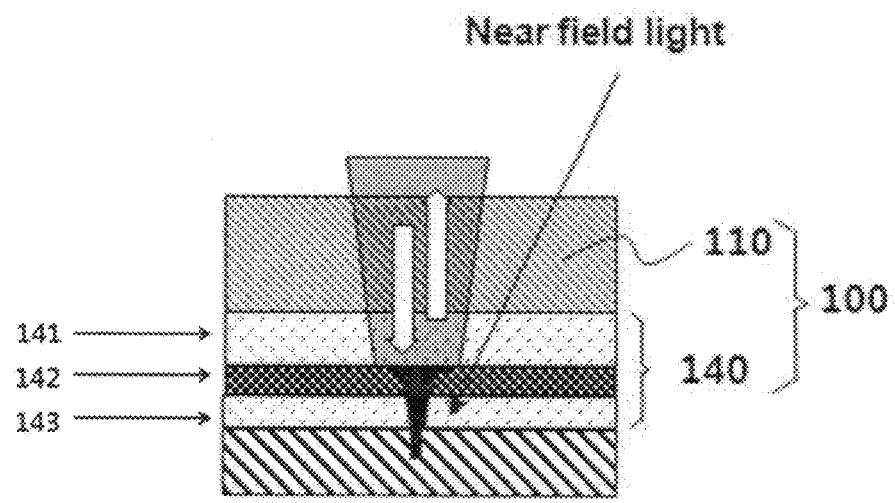
FIG. 8 is a sectional view showing an optical head having a flexible nano film according to the present invention.

FIG. 6 is a sectional view showing an optical head having a nano-hole structure according to the present invention, FIG. 7 is a sectional view showing an optical head having a nano-dot structure according to the present invention, and FIG. 8 is a sectional view showing an optical head having a flexible nano film according to the present invention. As shown in FIGS. 6 to 8, the nano-structure array includes any one selected from the group consisting of a nano-hole array 120, a nano-island array, a nano-pillar array, a nano-line array, and a nano-dot array 130.

Further, the nano-structure array includes a metal array formed of any one selected from the group consisting of Au, Ag, Pt, Cr and Al.

The flexible nano film 140 includes a first dielectric protective layer 141 formed on top thereof, a second dielectric protective layer 143 formed on bottom thereof, and a layer for formation of dynamic optical nano apertures 142 formed between the first dielectric protective layer 141 and the second dielectric protective layer 143. The flexible nano film 140 allows the light collected from the microlenses to pass through the layer for formation of dynamic optical nano apertures 142 surrounded with the first dielectric protective layer 141 and the second dielectric protective layer 143, thus reducing the focused region of the light. At this time, the first dielectric protective layer 141 serves to prevent the generation of degradation and mixing caused by the inter-diffusion between the layer for formation of dynamic optical nano apertures 142 and the flexible substrate 110, and the second dielectric protective layer 143 serves as an air gap to maintain a given distance between the flexible nano film 140 and the measured object 300.

The first dielectric protective layer 141 and the second dielectric protective layer 143 are made of oxide-based materials, nitride-based materials, carbide-based materials, or chalcogenide-based materials, wherein the oxide-based materials include SiOx, ZnS—SiOx, GeOx, AlOx, BeOx, ZrOx, BaTiOx, SrTiOx, TaOx and the like, and the nitride-based materials include SiNx, BNx, AlNx and the like. Further, the carbide-based materials include SiCx and the like, and the chalcogenide-based materials include ZnS, ZnSe and the like. Among the materials, the ZnS—SiO$_2$ maintains a high temperature and a high mechanical strength, while having a low degree of thermal deformation, thus being used most appropriately as the first dielectric protective layer 141 and the second dielectric protective layer 143.

In case of the structure of the flexible nano film 140, if the focus of far field optics is located on the layer for formation of dynamic optical nano apertures 142, the temperature of the layer for formation of dynamic optical nano apertures 142 is raised to form instant or permanent dynamic optical nano apertures on a material for formation of dynamic optical nano apertures, whereas a region having locally different optical characteristics is formed due to the changes of the optical characteristics of the material for formation of dynamic optical nano apertures. The region having locally different optical characteristics is smaller than the focus size of the far field optics and also utilized as a near-field revelation structure under the principle where near field is formed therein.

The flexible substrate 110 includes any one selected from the group consisting of PC, COP, PI, PET, OPP, PE, PP, PMMA, and acrylic films, or any one selected from the group consisting of sodalime glass, borosilicate glass, fused silica glass, quartz glass, and biocompatible polymers (for example, PLA, PGA, PLGA, LPLA, DUPLA, PCL, PDO and PDMS).

Further, the flexible substrate 110 includes a nano lubricating layer formed on the underside thereof to prevent friction and contamination of the measured object 300.

According to the present invention, the first dielectric protective layer 141 of the flexible nano film 140, which helps the formation of the dynamic optical nano apertures, has a thickness in the range of 30 to 500 nm. If the layer for formation of dynamic optical nano apertures 142 is high in thickness, the light transmittance thereof becomes low, and therefore, the layer for formation of dynamic optical nano apertures 142 has a thickness in the range of 5 to 30 nm.

Further, the second dielectric protective layer 143 of the flexible nano film 140, which helps the formation of the dynamic optical nano apertures of the layer for formation of dynamic optical nano apertures 142, requires a low thickness for the near-field revelation, so that it has a thickness in the range of 5 to 60 nm.

Further, since the films require a thickness having given elasticity for bonding to a curved or flat surface, it has a thickness in the range of 0.04 to 500 um, and only if the glass has an optical focal length allowed, it does not have any limitation in thickness.

Figure 9:
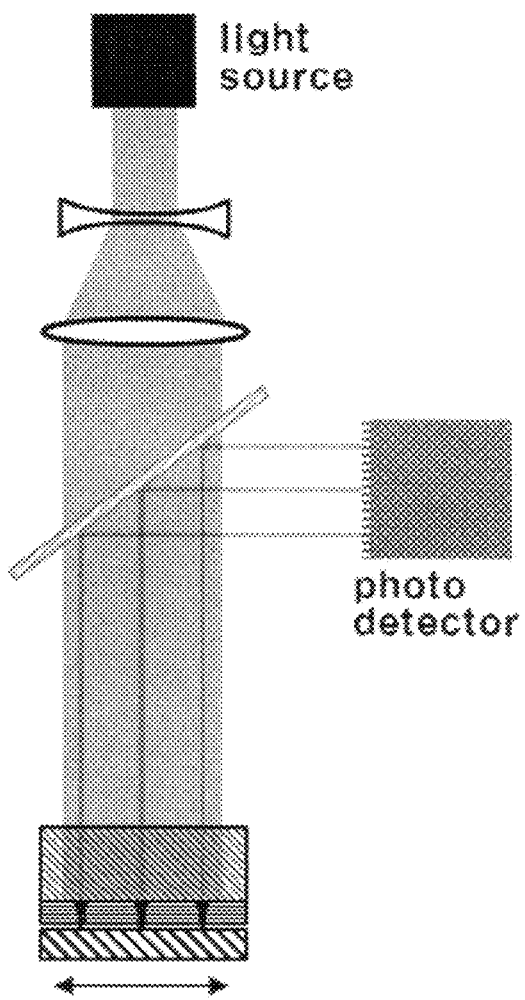
FIG. 9 is a sectional view showing the state wherein the light reflected from a measured object is detected by a photo detector in the near-field optical imaging device according to the present invention.
Figure 10:
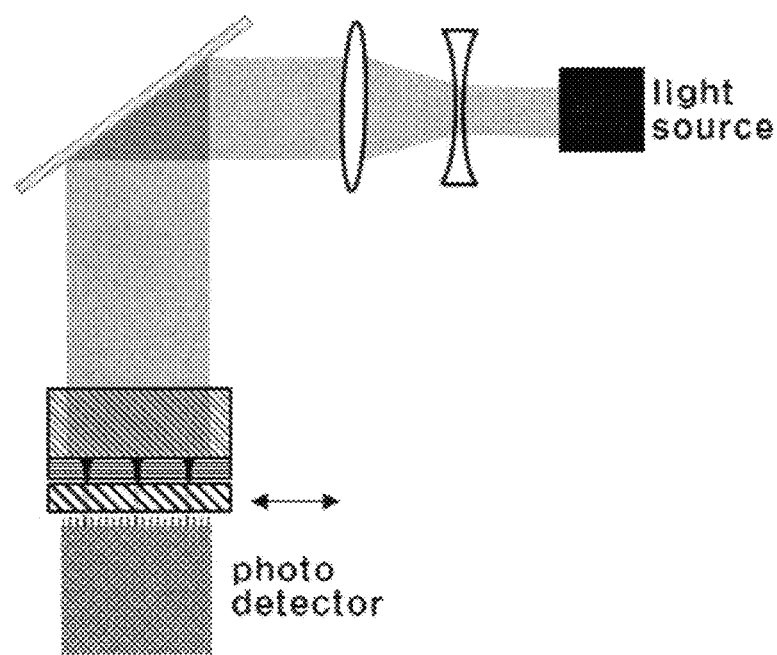
FIG. 10 is a sectional view showing the state wherein the light passing through a measured object is detected by a photo detector in the near-field optical imaging device according to the present invention.

FIG. 9 is a sectional view showing the state wherein light reflected from a measured object is detected by a photo detector in the near-field optical imaging device according to the present invention, and FIG. 10 is a sectional view showing the state wherein light passing through a measured object is detected by a photo detector in the near-field optical imaging device according to the present invention. As shown in FIGS. 9 and 10, if the thickness of the measured object is so high that light is reflected therefrom, the reflected light can be detected by means of the photo detector. At this time, the photo detector just reflects the light reflected from the measured object through a mirror and the like to detect the reflected light, so that the photo detector is not specially limited in position thereof.

Further, the near-field optical imaging device according to the present invention is applied to Raman spectroscopy using both of the light reflected from the measured object and the light scattered therefrom and further to detect the fluorescent signal of the measured object. At this time, the photo detector separately includes a spectrometer and a cut-off filter according to the characteristics of light to be measured.

Further, the photo detector is located under the measured object to detect a transmitted or scattered signal and a fluorescent signal generated from the measured object through the near-field light source, and infrared spectroscopy, Raman spectroscopy, fluorescence analysis and the like are adopted through the photo detector having the spectrometer or the cut-off filter.

Further, if the photo detector is located under the measured object, a separate optical system and driver for detection may be utilized.

Figure 11A:
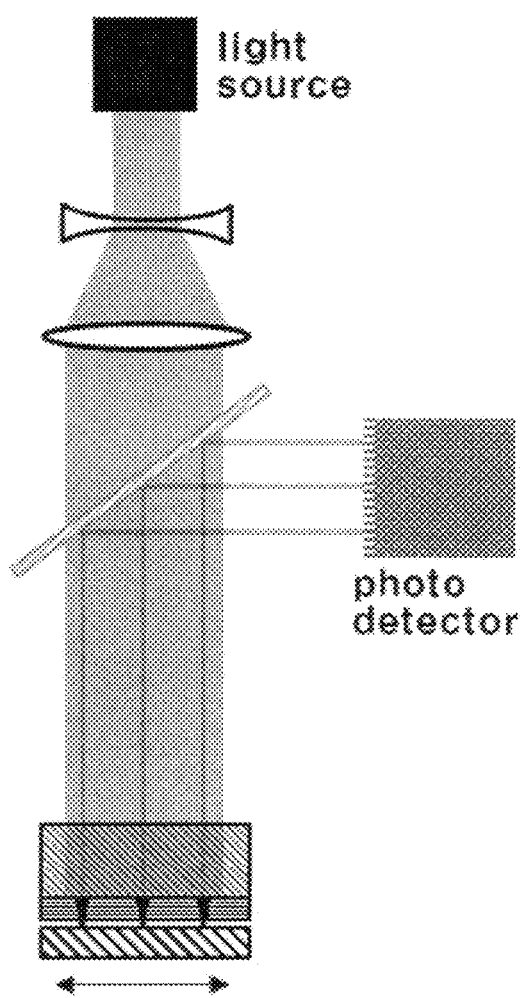
Figure 11B:
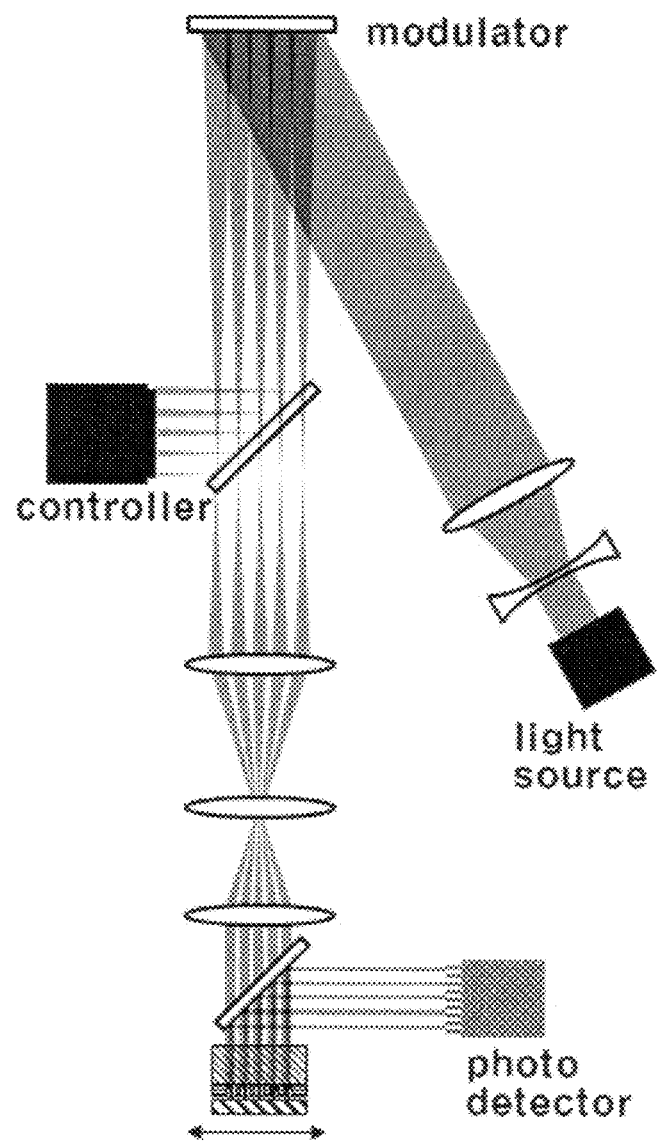
Figure 11C:
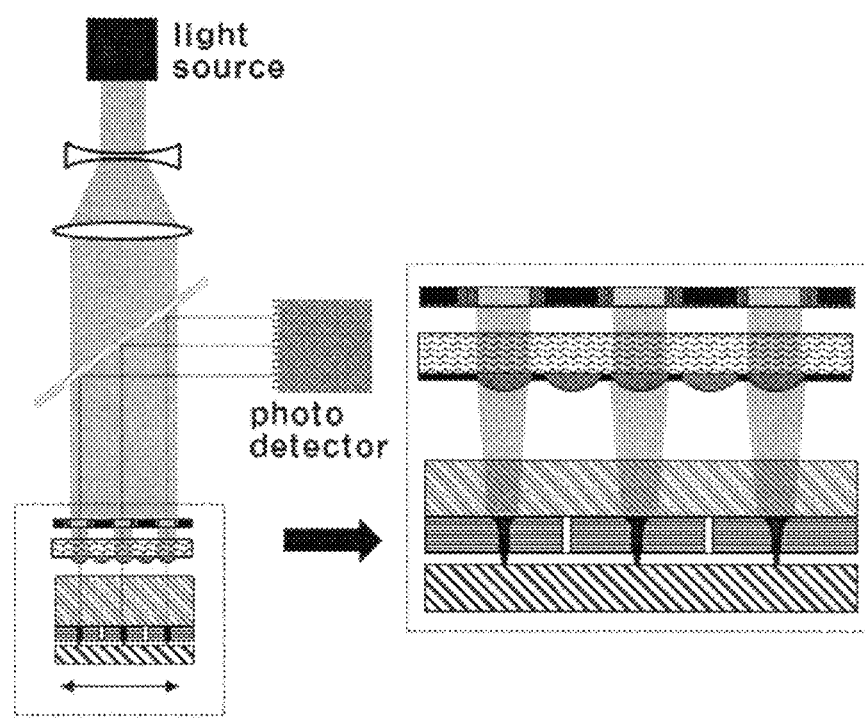

FIGS. 11A to 11C are sectional views showing multi-light arrays applied to the near-field optical imaging device according to the present invention, wherein FIG. 11A shows a macro optical system, FIG. 11B a hologram light modulator, and FIG. 11C a microlens array.

As shown in FIGS. 11A to 11C, various types of multi-light arrays are used. Large-area imaging can be conducted through the multi-light array, and further, individual light source of the multi-light array can be controlled independently of each other.

Figure 12:
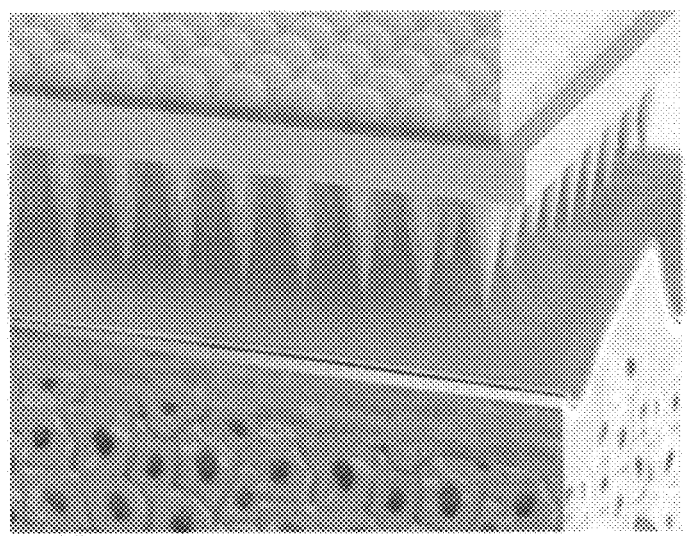
FIG. 12 is a perspective view showing the separated state between the multi-light array and the optical head in the near-field optical imaging device according to the present invention.
Figure 13:
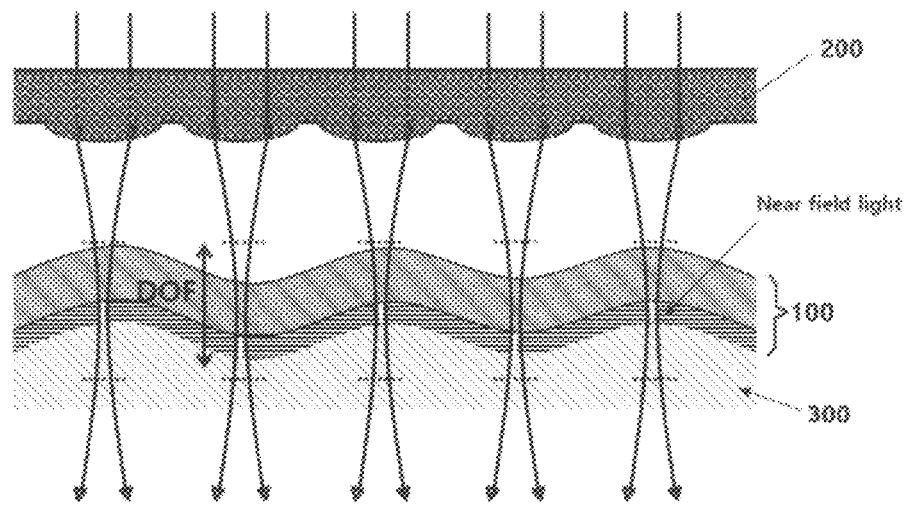
FIG. 13 is a front view showing the separated state between the multi-light array and the optical head in the near-field optical imaging device according to the present invention.

FIG. 12 is a perspective view showing the separated state between the multi-light array and the optical head in the near-field optical imaging device according to the present invention, and FIG. 13 is a front view showing the separated state between the multi-light array and the optical head in the near-field optical imaging device according to the present invention.

As shown in FIGS. 12 and 13, the optical head 100 having the flexible substrate 110 is located on the measured object 300, without having any gap, and the light passing through the multi-light array 200 reveals the near field on the near-field revelation part of the optical head 100, thus easily measuring the measured object 300 having the curved shape.

Figure 14:
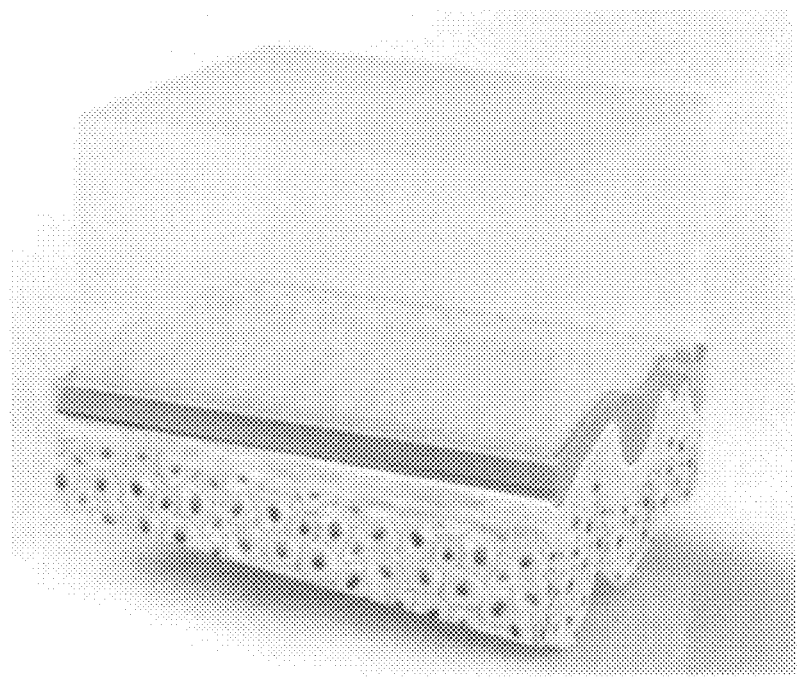
FIG. 14 is a perspective view showing the integral state between the multi-light array and the optical head in the near-field optical imaging device according to the present invention.
Figure 15:
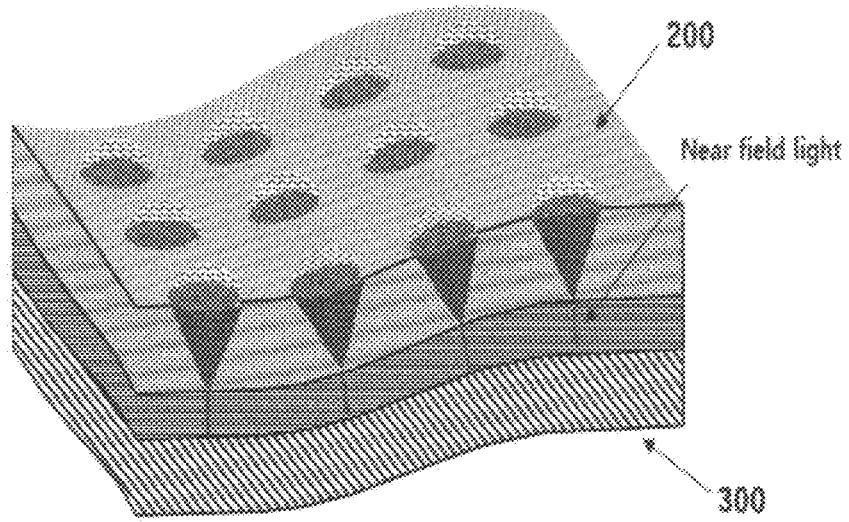
FIG. 15 is a front view showing the integral state between the multi-light array and the optical head in the near-field optical imaging device according to the present invention.

FIG. 14 is a perspective view showing the integral state between the multi-light array and the optical head in the near-field optical imaging device according to the present invention, and FIG. 15 is a front view showing the integral state between the multi-light array and the optical head in the near-field optical imaging device according to the present invention.

As shown in FIGS. 14 and 15, the multi-light array 200 and the optical head 100 are coupled integrally with each other, and through the coupling, the region of the light collected on the photo detector becomes expanded, thus allowing the imaging device to be easily applied to the measured object having a large curved angle. Therefore, it is possible to conduct large area curved nano imaging.

As described above, the optical head and the imaging device according to the present invention are configured wherein the near field is revealed by using the near-field revelation part, thus making it possible to conduct high resolution, and wherein the flexible substrate is flexibly deformed in such a manner as to be easily brought into close contact with the measured object even if the measured object has a curved or flat shape, thus solving the existing gap-maintaining problem.

Further, the near-field revelation part includes the layer for formation of dynamic optical nano apertures 142 or the metal nano structure, so that within the focal region of the far field optics, it is possible to reveal near field through the change of a material for formation of dynamic optical nano apertures from optically non-transparent phase to optically transparent phase or through the localized surface plasmon effects of the nano structure formed on the near-field revelation part.

Furthermore, the optical head includes the nano lubricating layer formed on the underside thereof to prevent the friction and contamination of the measured object.

Additionally, the imaging device according to the present invention is provided with the multi-light array, thus making it possible to conduct large area imaging.

Moreover, the multi-light array and the optical head are coupled integrally with each other, and through the coupling, the region of the light collected on the photo detector becomes expanded, thus allowing the imaging device to be easily applied to the measured object having a large curved angle.

Further, the light reflected from the measured object is detected through the photo detector, and if the light is not reflected from the measured object whose thickness is relatively low, the photo detector is located below the measured object, thus detecting the light passing through the measured object.

Furthermore, the light reflected or scattered from the measured object, the fluorescence signal generated from the measured object, or non-linear optical signal (for example, Raman scattering, two-photon fluorescence, or second harmonic generation) is detected through the multi-light array and the photo detector.

In addition, the photo detector is located below the measured object if necessary, thus detecting the light transmitted to or scattered from the measured object, the fluorescence signal generated from the measured object, or non-linear optical signal (for example, Raman scattering, two-photon fluorescence, or second harmonic generation).

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. An optical head for revealing near field through beams irradiated from a light source of a far field optical system, the optical head comprising:
    a flexible substrate made of a soft material and adapted to allow the optical head to be brought into close contact with a measured object and attached thereto even if the measured object has a curved or flat surface; and
    a near-field revelation part located between the measured object and the flexible substrate in such a manner as to have one side brought into contact with the flexible substrate and the other side detachably attached to the measured object and adapted to reveal the near field through the beams irradiated from the light source,
    wherein the near-field revelation part comprises: a layer for formation of dynamic optical nano apertures; a first dielectric protective layer formed on top of the layer for formation of dynamic optical nano apertures to prevent the generation of degradation and mixing caused by the inter-diffusion between the layer for formation of dynamic optical nano apertures and the flexible substrate; and a second dielectric protective layer formed on the underside of the layer for formation of dynamic optical nano apertures to maintain a given distance between the layer for formation of dynamic optical nano apertures and the measured object.

2. An optical head for revealing near field through beams irradiated from a light source of a far field optical system, the optical head comprising:
    a flexible substrate made of a soft material and adapted to allow the optical head to be brought into close contact with a measured object and attached thereto even if the measured object has a curved or flat surface; and
    a near-field revelation part located between the measured object and the flexible substrate in such a manner as to have one side brought into contact with the flexible substrate and the other side detachably attached to the measured object and adapted to reveal the near field through the beams irradiated from the light source, wherein the near-field revelation part comprises a nano-structure array.

3. The optical head according to claim 1, wherein the optical system comprises any one selected from the group consisting of a macro optical system, a hologram light modulator, a DMD mirror, a microlens array, and a scanner.

4. The optical head according to claim 1, wherein the flexible substrate and the near-field revelation part are formed integrally with each other.

5. The optical head according to claim 2, wherein the nano-structure array comprises any one selected from the group consisting of a nano-hole array, a nano-island array, a nano-pillar array, a nano-line array, and a nano-dot array.

6. The optical head according to claim 2, wherein the nano-structure array comprises a metal array formed of any one selected from the group consisting of Au, Ag, Pt, Cr and Al.

7. The optical head according to claim 1, wherein the near-field revelation part is a flexible nano film.

8. The optical head according to claim 1, wherein the layer for formation of dynamic optical nano apertures is made of a chalcogenide-based material.

9. The optical head according to claim 1, wherein the layer for formation of dynamic optical nano apertures is made of AgOx or PtOx.

10. The optical head according to claim 1, wherein the first dielectric protective layer and the second dielectric protective layer are made of an oxide-based material, a nitride-based material, a carbide-based material, or a chalcogenide-based material.

11. The optical head according to claim 10, wherein the oxide-based material comprises any one selected from the group consisting of SiOx, ZnS—SiOx, GeOx, AlOx, BeOx, ZrOx, BaTiOx, SrTiOx, and TaOx.

12. The optical head according to claim 10, wherein the nitride-based material comprises any one selected from the group consisting of SiNx, BNx, and AlNx.

13. The optical head according to claim 10, wherein the carbide-based material comprises SiCx.

14. The optical head according to claim 10, wherein the chalcogenide-based material comprises any one selected from the group consisting of ZnS and ZnSe.

15. The optical head according to claim 1, wherein the flexible substrate comprises any one selected from the group consisting of PC, COP, PI, PET, OPP, PE, PP, PMMA, and acrylic films, or any one selected from the group consisting of sodalime glass, borosilicate glass, fused silica glass, quartz glass, and biocompatible polymers (such as PLA, PGA, PLGA, LPLA, DUPLA, PCL, PDO and PDMS).

16. The optical head according to claim 1, wherein the first dielectric protective layer has a thickness in the range of 30 to 500 nm, the layer for formation of dynamic optical nano apertures has a thickness in the range of 5 to nm, and the second dielectric protective layer has a thickness in the range of 5 to 60 nm.

17. The optical head according to claim 15, wherein the films have a thickness in the range of 0.04 to 500 um.

18. The optical head according to claim 1, further comprising a nano lubricating layer formed on the underside thereof to prevent friction and contamination of the measured object.

19. A near-field optical imaging device comprising:
a light source irradiating light therefrom;
a relay lens unit having one or more lenses adapted to pass the light transmitted to a measured object or reflected from the measured object therethrough and to focus the light irradiated from the light source thereon;
a multi-light array adapted to allow the light focused by the relay lens unit to be incident thereon;
an optical head adapted to reveal near field on the beams irradiated from the light source of a far-field optical system passing through the multi-light array; and
a photo detector adapted to detect the light reflected from the measured object,
wherein the optical head comprises: a flexible substrate made of a soft material and adapted to allow the optical head to be brought into close contact with the measured object and attached thereto even if the measured object has a curved or flat surface; and a near-field revelation part located between the measured object and the flexible substrate in such a manner as to have one side brought into contact with the flexible substrate and the other side detachably attached to the measured object and adapted to reveal the near field through the beams irradiated from the light source.

20. The near-field optical imaging device according to claim 19, wherein the multi-light array comprises any one selected from the group consisting of a macro optical system, a hologram light modulator, a DMD mirror, a microlens array, and a scanner.

21. The near-field optical imaging device according to claim 19, wherein the flexible substrate and the near-field revelation part are formed integrally with each other.

22. The near-field optical imaging device according to claim 19, wherein the near-field revelation part comprises a nano-structure array.

23. The near-field optical imaging device according to claim 22, wherein the nano-structure array comprises any one selected from the group consisting of a nano-hole array, a nano-island array, a nano-pillar array, a nano-line array, and a nano-dot array.

24. The near-field optical imaging device according to claim 22, wherein the nano-structure array comprises a metal array formed of any one selected from the group consisting of Au, Ag, Pt, Cr and Al.

25. The near-field optical imaging device according to claim 19, wherein the near-field revelation part comprises a flexible nano film.

26. The near-field optical imaging device according to claim 25, wherein the flexible nano film comprises: a first dielectric protective layer formed on top of thereof; a second dielectric protective layer formed on the underside thereof; and a layer for formation of dynamic optical nano apertures formed between the first dielectric protective layer and the second dielectric protective layer.

27. The near-field optical imaging device according to claim 26, wherein the layer for formation of dynamic optical nano apertures is made of a chalcogenide-based material.

28. The near-field optical imaging device according to claim 26, wherein the layer for formation of dynamic optical nano apertures is made of AgOx or PtOx.

29. The near-field optical imaging device according to claim 26, wherein the first dielectric protective layer and the second dielectric protective layer are made of an oxide-based material, a nitride-based material, a carbide-based material, or a chalcogenide-based material.

30. The near-field optical imaging device according to claim 29, wherein the oxide-based material comprises any one selected from the group consisting of SiOx, ZnS—SiOx, GeOx, AlOx, BeOx, ZrOx, BaTiOx, SrTiOx, and TaOx.

31. The near-field optical imaging device according to claim 29, wherein the nitride-based material comprises any one selected from the group consisting of SiNx, BNx, and AlNx.

32. The near-field optical imaging device according to claim 29, wherein the carbide-based material comprises SiCx.

33. The near-field optical imaging device according to claim 29, wherein the chalcogenide-based material comprises any one selected from the group consisting of ZnS and ZnSe.

34. The near-field optical imaging device according to claim 19, wherein the flexible substrate comprises any one selected from the group consisting of PC, COP, PI, PET, OFF, PE, PP, PMMA, and acrylic films, or any one selected from the group consisting of sodalime glass, borosilicate glass, fused silica glass, quartz glass, and biocompatible polymers (such as PLA, PGA, PLGA, LPLA, DUPLA, PCL, PDO and PDMS).

35. The near-field optical imaging device according to claim 26, wherein the first dielectric protective layer has a thickness in the range of 30 to 500 nm, the layer for formation of dynamic optical nano apertures has a thickness in the range of 5 to 30 nm, and the second dielectric protective layer has a thickness in the range of 5 to 60 nm.

36. The near-field optical imaging device according to claim 34, wherein the films have a thickness in the range of 0.04 to 500 um.

37. The near-field optical imaging device according to claim 19, further comprising a nano lubricating layer formed on the underside of the optical head to prevent friction and contamination of the measured object.

38. The near-field optical imaging device according to claim 19, wherein the multi-light array and the optical head are formed integrally with each other.

39. The near-field optical imaging device according to claim 19, wherein the photo detector measures Raman scattering generated from the measured object.

40. The near-field optical imaging device according to claim 39, wherein the photo detector comprises a spectrometer in such a manner as to be applied to Raman spectroscopy through the spectrum of the Raman scattering.

41. The near-field optical imaging device according to claim 19, wherein the photo detector measures two-photon fluorescence and second harmonic generation from the measured object.

42. The near-field optical imaging device according to claim 41, wherein the photo detector comprises a cut-off filter adapted to cut off excitation light to measure the two-photon fluorescence from the measured object.

43. The near-field optical imaging device according to claim 19, wherein the photo detector is located below the measured object to detect the light passing through the measured object.

44. The near-field optical imaging device according to claim 43, wherein the photo detector comprises a spectrometer in such a manner as to be applied to infrared spectroscopy through the spectrum of the transmitted light.

45. The near-field optical imaging device according to claim 19, wherein the photo detector is located below the measured object to detect Raman scattering from the measured object.

46. The near-field optical imaging device according to claim 45, wherein the photo detector comprises a spectrometer in such a manner as to be applied to Raman spectroscopy through the spectrum of the Raman scattering.

47. The near-field optical imaging device according to claim 19, wherein the photo detector is located below the measured object to detect two-photon fluorescence from the measured object.

48. The near-field optical imaging device according to claim 47, wherein the photo detector comprises a cut-off filter adapted to cut off excitation light to measure the two-photon fluorescence from the measured object.

49. The optical head according to claim 2, wherein the optical system comprises any one selected from the group consisting of a macro optical system, a hologram light modulator, a DMD mirror, a microlens array, and a scanner.

50. The optical head according to claim 2, wherein the flexible substrate and the near-field revelation part are formed integrally with each other.

51. The optical head according to claim 2, wherein the flexible substrate comprises any one selected from the group consisting of PC, COP, PI, PET, OPP, PE, PP, PMMA, and acrylic films, or any one selected from the group consisting of sodalime glass, borosilicate glass, fused silica glass, quartz glass, and biocompatible polymers (such as PLA, PGA, PLGA, LPLA, DUPLA, PCL, PDO and PDMS).

52. The optical head according to claim 2, further comprising a nano lubricating layer formed on the underside thereof to prevent friction and contamination of the measured object.

* * * * *